(12) United States Patent
Conley et al.

(10) Patent No.: US 8,937,036 B2
(45) Date of Patent: Jan. 20, 2015

(54) CLEANING, DISINFECTING, DEODORIZING, AND BLEACHING COMPOSITION FOR REMOVABLE DENTAL APPLIANCES

(71) Applicants: Nicholas Conley, Cupertino, CA (US); Lynn Muzik, Cupertino, CA (US)

(72) Inventors: Nicholas Conley, Cupertino, CA (US); Lynn Muzik, Cupertino, CA (US)

(73) Assignee: LMA Solutions Inc., Cupertino, CA (US)

( * ) Notice: Subject to any disclaimer, the term of this patent is extended or adjusted under 35 U.S.C. 154(b) by 0 days.

(21) Appl. No.: 14/213,672

(22) Filed: Mar. 14, 2014

(65) Prior Publication Data

US 2014/0287972 A1 Sep. 25, 2014

Related U.S. Application Data

(60) Provisional application No. 61/786,458, filed on Mar. 15, 2013.

(51) Int. Cl.
| | | |
|---|---|---|
| *C11D 3/395* | (2006.01) | |
| *C11D 7/34* | (2006.01) | |
| *A61K 8/44* | (2006.01) | |
| *A61Q 11/02* | (2006.01) | |
| *A61K 8/20* | (2006.01) | |

(52) U.S. Cl.
CPC . *A61K 8/44* (2013.01); *A61Q 11/02* (2013.01); *A61K 8/20* (2013.01)
USPC ........... 510/116; 510/117; 510/367; 510/379; 510/492; 510/494

(58) Field of Classification Search
USPC .................. 510/116, 117, 367, 379, 492, 494
See application file for complete search history.

(56) References Cited

U.S. PATENT DOCUMENTS

| | | | |
|---|---|---|---|
| 4,362,639 A | 12/1982 | Eoga | |
| 4,552,679 A | 11/1985 | Schobel et al. | |
| 4,568,560 A * | 2/1986 | Schobel | 424/401 |
| 5,486,304 A | 1/1996 | Eoga et al. | |
| 7,199,082 B1* | 4/2007 | Chapman et al. | 504/115 |
| 8,044,008 B2 | 10/2011 | Muzik et al. | |
| 2007/0054830 A1 | 3/2007 | Dullea et al. | |
| 2009/0042756 A1* | 2/2009 | Muzik et al. | 510/100 |
| 2012/0125847 A1* | 5/2012 | Sehgal | 210/639 |
| 2013/0323308 A1* | 12/2013 | Simpkins | 424/490 |
| 2014/0065627 A1* | 3/2014 | Whitney et al. | 435/6.12 |

\* cited by examiner

*Primary Examiner* — Charles Boyer
(74) *Attorney, Agent, or Firm* — Dale F. Regelman; Quarles & Brady LLP

(57) ABSTRACT

A dental appliance disinfecting composition which includes a chloramine bleaching agent and an amino acid.

10 Claims, No Drawings

CLEANING, DISINFECTING, DEODORIZING, AND BLEACHING COMPOSITION FOR REMOVABLE DENTAL APPLIANCES

CROSS REFERENCE TO RELATED APPLICATIONS

This Application claims priority from a U.S. Provisional Application filed Mar. 15, 2013 and having Ser. No. 61/786,458.

FIELD OF THE INVENTION

The invention described herein relates to a composition for cleaning, disinfecting, deodorizing, bleaching and removing plaque from dental appliances, such as retainers, night guards, removable braces, and dentures, and method using same.

BACKGROUND OF THE INVENTION

The accumulation of residues on dental appliances (e.g., removable braces, retainers, night guards, removable braces, dentures, etc.) is a familiar and persistent problem for wearers of such appliances. These residues often consist of some combination of food particles and biofilm (i.e., plaque), the latter of which is a slime layer that naturally develops when bacteria attach to an inert support. Many of these bacteria produce volatile sulfur compounds as waste products. If the dental appliance is not rid of food particles and biofilm on a regular basis, the malodourous waste products will accumulate, causing the wearer to exhibit bad breath. Even more serious is the potential for pathogenic bacteria to inhabit the biofilm, increasing the likelihood of infection for the wearer.

The majority of commercially available effervescent dental appliance cleansing tablets are based on alkaline peroxysalts (e.g., those sold under the tradename EFFERDENT), which provide excellent bleaching action but poor plaque removal, as described in U.S. Pat. No. 4,552,679. An additional shortcoming of alkaline peroxysalts is their documented health risk. After seventy-three severe reactions and at least one death, the U.S. Food and Drug Administration issued a statement on Feb. 14, 2008 asking the manufacturers of denture cleansers to revise labeling and to consider appropriate alternatives to persulfate, a common alkaline peroxysalt found in many brands, including EFFERDENT. All peroxysalts share a common mode of operation (i.e., liberation of hydrogen peroxide upon contact with water) and a similar structural feature (i.e., an associated molecule of hydrogen peroxide). Therefore, it is an object of the present invention to provide a dental appliance cleansing composition that does not include peroxysalts. Examples of powders and tablets incorporating alkaline peroxysalts can be found in U.S. Pat. Nos. 4,362,639, 4,552,679, and 5,486,304, and U.S. Patent Application 20070054830.

U.S. Pat. No. 8,044,008 to Muzik et al ("the Muzik composition") represents the most efficacious prior art composition. A shortcoming of the Muzik composition, however, is a high concentration of a chloramine bleaching agent, namely from 1 percent to 20 percent by weight of the composition. Upon dissolution of the composition in water, a pH-dependent equilibrium is established between the chloramine bleaching agent, hypochlorous acid, and hypochlorite ion. However, upon dissolution of the composition in water, hypochlorous acid also imparts a chlorine-like odor that is reminiscent of swimming pools. Muzik et al. teach the use of a fragrance at up to about 3 percent by weight of the composition "to mask any chlorine odor originating from the dental appliance cleansing formula." Unfortunately, high liquid fragrance loadings (greater than about 1.5 percent) can introduce aggregation of solids in the formula ("caking") and slow dissolution. In addition, fragrance represents one of the most expensive raw materials costs in the manufacture of the composition. Therefore, a need persists for a composition that is effective at disinfecting and removing biofilm from dental appliances without suffering from the shortcomings of chlorine-like odor and/or the requirement for high fragrance loadings.

DETAILED DESCRIPTION OF PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Applicants' composition represents a significant improvement over the prior art, particularly Muzik et al. To remedy deficiencies in the prior art, Applicants' improved composition comprises (a) a chloramine bleaching agent, (b) a surfactant, (c) a water-soluble carboxylic acid, (d) an alkaline base (e) a chelating agent for alkaline earth metal ions, and (f) an amino acid.

Optional components may be added to the composition to facilitate its storage and handling, and to make it more pleasing to the user. These optional components include, but are not limited to, a fragrant substance, an indicator dye, an anti-caking agent, a tablet binder, and a lubricant.

In certain embodiments, Applicants' "amino" acid comprises an amino-substituted alkyl sulfonic acid I.

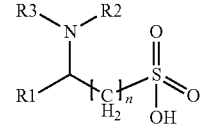

In certain embodiments, R1 is selected from the group consisting of —H, —CH$_3$, and phenyl. In certain embodiments, R2 is selected from the group consisting of —H, alkyl, and phenyl. In certain embodiments, R3 is selected from the group consisting of —H, alkyl, and phenyl. In certain embodiments, n is 0 to about 4.

In certain embodiments, the amino moiety of Applicants' amino-substituted alkyl sulfonic acid component comprises a secondary amine. In certain embodiments, the amino moiety of Applicants' amino-substituted alkyl sulfonic acid comprises a tertiary amine.

In certain embodiments, the —N(R2)(R3) moiety of Applicants' amino-substituted alkyl sulfonic acid comprises a cyclic structure. In certain embodiments, the —N(R2)(R3) moiety of Applicants' amino-substituted alkyl sulfonic acid comprises a morpholino group. In certain embodiments, the —N(R2)(R3) moiety of Applicants' amino-substituted alkyl sulfonic acid comprises a pyrrolidino group. In certain embodiments, the —N(R2)(R3) moiety of Applicants' amino-substituted alkyl sulfonic acid comprises a piperidino group. In certain embodiments, the —N(R2)(R3) moiety of Applicants' amino-substituted alkyl sulfonic acid comprises a piperazino group.

In certain embodiments, amino-sulfonic acid I comprises 3-(N-morpholino)propanesulfonic acid ("MOPS"), wherein R1 is —H, R2 and R3 in combination comprise —N morpholino, and n is 2. In certain embodiments, amino-sulfonic acid I comprises 2-(N-morpholino)ethanesulfonic acid ("MES"), wherein R1 is —H, R2 and R3 in combination comprise —N morpholino, and n is 1.

In certain embodiments, Applicants' composition comprises from about 0.001 percent to about 20 percent by weight of the MOPS and/or MES additive. In certain embodiments, Applicants' composition comprises from about 0.02 percent to about 10 percent by weight of the MOPS and/or MES additive. In certain embodiments, Applicants' composition comprises from about 0.015 percent to about 0.025 percent by weight of the MOPS and/or MES additive.

The "chloramine bleaching agent" is any chemical compound containing one or more chlorine-nitrogen bonds that liberates hypochlorous acid upon contact with water. Examples of chloramine bleaching agents include, but are not limited to, sodium dichloroisocyanurate and sodium trichloroisocyanurate, and include both the salt and acid forms. Other chloramine bleaching agents are well known in the art and are equally suitable. In certain embodiments, Applicants' composition comprises from about 0.01 percent to about 20 percent by weight of the chloramine bleaching agent. In certain embodiments, Applicants' composition comprises from about 0.2 percent to about 10 percent by weight of the chloramine bleaching agent. In certain embodiments, Applicants' composition comprises from about 0.4 percent to about 0.6 percent by weight of the chloramine bleaching agent.

The "surfactant" is any organic compound that contains at least one hydrophobic functional group and one hydrophilic functional group (i.e., an amphiphilic compound). The surfactants may be ionic or non-ionic in nature. Examples of surfactants include, but are not limited to, sodium dodecyl sulfate, sodium laureth sulfate, sodium dodecylbenzenesulfonate, alkyl polyl(ethylene oxide), and cetyl alcohol. Other surfactants are well known in the art and are equally suitable. In certain embodiments, Applicants' composition comprises from about 0.1 percent to about 10 percent by weight of the surfactant. In certain embodiments, Applicants' composition comprises from about 2 percent to about 5 percent by weight of the surfactant. In certain embodiments, Applicants' composition comprises from about 3.5 percent to about 4.5 percent by weight of the surfactant.

The "water-soluble carboxylic acid" is any compound containing one or more carboxylic acid functional groups (i.e., —COOH) and a solubility in water greater than about 20 g/L. Examples of suitable carboxylic acids include, but are not limited to, oxalic acid, malonic acid, malic acid, maleic acid, and citric acid. Other water-soluble carboxylic acids are well known in the art and are equally suitable. In certain embodiments, Applicants' composition comprises from about 70 percent by weight of the water-soluble carboxylic acid. In certain embodiments, Applicants' composition comprises from about 30 percent to about 50 percent by weight of the water-soluble carboxylic acid. In certain embodiments, Applicants' composition comprises from about 40 percent to about 44 percent by weight of the water-soluble carboxylic acid.

The "alkaline base" is the basic salt of any alkali metal or alkaline earth metal. Examples of suitable alkaline bases include, but are not limited to, sodium carbonate, sodium bicarbonate, sodium hydroxide, potassium carbonate, potassium bicarbonate, potassium hydroxide, calcium carbonate, and magnesium hydroxide. Other alkaline bases are well known in the art and are equally suitable. It should be noted that the alkaline base need not be soluble in water.

In certain embodiments, Applicants' composition comprises from about 5 percent to about 40 percent by weight of the alkaline base. In certain embodiments, Applicants' composition comprises from about 22 percent to about 32 percent by weight of the alkaline base. In certain embodiments, Applicants' composition comprises from about 26 percent to about 28 percent by weight of the alkaline base.

The "chelating agent" is any compound that binds to alkaline earth metal ions, especially calcium and magnesium, and forms a complex that exhibits some degree of water solubility. Examples of suitable chelating agents include, but are not limited to, tetrasodium pyrophosphate, sodium tripolyphosphate, sodium tetraphosphate, sodium hexametaphosphate, ethylenediaminetetraacetic acid, and ethylene glycol tetraacetic acid. Other chelating agents are well known in the art and are equally suitable. In certain embodiments, Applicants' composition comprises from about 1 percent to about 30 percent by weight of the chelating agent. In certain embodiments, Applicants' composition comprises from about 10 percent to about 20 percent by weight of the chelating agent. In certain embodiments, Applicants' composition comprises from of about 14 percent to about 16 percent by weight of the chelating agent.

Applicants have found that the amino acid component dramatically potentiates the disinfecting properties of the chloramine bleaching agent, allowing the latter to be incorporated at lower percentages, which reduces the chlorine-like odor of the composition upon dissolution in water.

It is also believed that the amino moiety of the amino-acid forms an N—Cl bond with chlorine from hypochlorous acid (formed upon dissolution of the composition in water) and reduces the concentration of the hypochlorous acid species, which is responsible for the chlorine-like odor.

The following examples are presented to further illustrate to persons skilled in the art how to make and use the invention. These examples are not intended as a limitation, however, upon the scope of the invention.

EXAMPLE I

The composition recited in Table 1 was used in this Example I.

TABLE 1

| COMPONENT | GRAMS Per Dose |
|---|---|
| Sodium Dichloroisocyanurate | 0.013 |
| Sodium Dodecyl Sulfate | 0.096 |

TABLE 1-continued

| COMPONENT | GRAMS Per Dose |
|---|---|
| Anhydrous Citric Acid | 1.057 |
| Anhydrous Sodium Carbonate | 0.673 |
| Sodium Tripolyphosphate | 0.384 |
| Anhydrous Sodium Sulfate | 0.248 |
| 2-(N-Morpholino)Ethanesulfonic Acid | 0.00048 |

To the composition was added 100 ml of tap water, and vigorous effervescence occurred. A DOCTOR'S brand plastic night guard, which was coated with an accumulated layer of biofilm from normal wear, was added to this solution. After 5 minutes, the appliance was removed, rinsed briefly with water, and stained with an FD&C Red 20 plaque disclosing dye tablet. No staining was noted, indicating that the biofilm had been removed by soaking in a solution of the composition.

A nearly identical night guard was used as a positive control (it was soaked in plain tap water only) and showed extensive staining

EXAMPLE II

The composition recited in Table 2 was used in this Example II.

TABLE 2

| COMPONENT | GRAMS Per Dose |
|---|---|
| Sodium Dichloroisocyanurate | 0.013 |
| Sodium Dodecyl Sulfate | 0.096 |
| Anhydrous Citric Acid | 1.057 |
| Anhydrous Sodium Carbonate | 0.673 |
| Sodium Tripolyphosphate | 0.384 |
| Anhydrous Sodium Sulfate | 0.248 |
| 2-(N-Morpholino)Ethanesulfonic Acid | 0.00048 |
| FD&C Blue No. 2/Indigo Carmine | 0.004 |
| Peppermint Oil | 0.025 |

To the composition was added 100 ml of tap water, and vigorous effervescence occurred, accompanied by the rapid appearance of blue color to the solution and almost equally rapid bleaching of the blue color. A DOCTOR'S brand plastic night guard, which was coated with an accumulated layer of biofilm from normal wear, was added to this solution. After 5 minutes, the appliance was removed, rinsed briefly with water, and stained with an FD&C Red 20 plaque disclosing dye tablet. No staining was noted, indicating that the biofilm had been removed by soaking in a solution of the composition.

A nearly identical night guard was used as a positive control (it was soaked in plain tap water only) and showed extensive staining.

EXAMPLE 3

The composition recited in Table 3 was used in this Example III.

TABLE 3

| COMPONENT | GRAMS Per Dose |
|---|---|
| Sodium Dichloroisocyanurate | 0.013 |
| Sodium Dodecyl Sulfate | 0.096 |
| Anhydrous Citric Acid | 1.057 |

TABLE 3-continued

| COMPONENT | GRAMS Per Dose |
|---|---|
| Anhydrous Sodium Carbonate | 0.673 |
| Sodium Tripolyphosphate | 0.384 |
| Anhydrous Sodium Sulfate | 0.248 |
| 3-(N-morpholino)Propanesulfonic acid | 0.00048 |

To the composition was added 100 ml of tap water, and vigorous effervescence occurred. A DOCTOR'S brand plastic night guard, which was coated with an accumulated layer of biofilm from normal wear, was added to this solution. After 5 minutes, the appliance was removed, rinsed briefly with water, and stained with an FD&C Red 20 plaque disclosing dye tablet. No staining was noted, indicating that the biofilm had been removed by soaking in a solution of the composition.

A nearly identical night guard was used as a positive control (it was soaked in plain tap water only) and showed extensive staining.

EXAMPLE IV

The composition recited in Table 4 was used in this Example IV.

TABLE 4

| COMPONENT | GRAMS Per Dose |
|---|---|
| Sodium Dichloroisocyanurate | 0.013 |
| Sodium Dodecyl Sulfate | 0.096 |
| Anhydrous Citric Acid | 1.057 |
| Anhydrous Sodium Carbonate | 0.673 |
| Sodium Tripolyphosphate | 0.384 |
| Anhydrous Sodium Sulfate | 0.248 |
| 3-(N-morpholino)propanesulfonic acid | 0.00048 |
| FD&C Blue No. 2/Indigo Carmine | 0.004 |
| Peppermint Oil | 0.025 |

To the composition was added 100 ml of tap water, and vigorous effervescence occurred, accompanied by the rapid appearance of a blue color to the solution. A DOCTOR'S brand plastic night guard, which was coated with an accumulated layer of biofilm from normal wear, was added to this solution. After 5 minutes, the appliance was removed, rinsed briefly with water, and stained with an FD&C Red 20 plaque disclosing dye tablet. No staining was noted, indicating that the biofilm had been removed by soaking in a solution of the composition.

A nearly identical night guard was used as a positive control (it was soaked in plain tap water only) and showed extensive staining While the preferred embodiments of the present invention have been illustrated in detail, it should be apparent that modifications and adaptations to those embodiments may occur to one skilled in the art without departing from the scope of the present invention as set forth herein.

We claim:

1. A method for cleaning, disinfecting, deodorizing, and bleaching removable dental appliances, comprising:

forming an aqueous solution of a disinfecting composition comprising a chloramine bleaching agent and an amino-substituted alkylsulfonic acid;

placing said removable dental appliance in said aqueous solution; and after about 5 minutes, removing said removable dental appliance from said aqueous solution, wherein said amino-substituted alkylsulfonic acid comprises the structure:

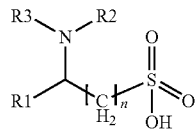

and wherein R1 is selected from the group consisting of —H, —CH₃, and phenyl, R2 is selected from the group consisting of —H, alkyl, and phenyl, R3 is selected from the group consisting of —H, alkyl, and phenyl, and n is 0 to about 4.

2. The method of claim 1, wherein an amino moiety of said amino-substituted alkyl sulfonic acid comprises a secondary amine.

3. The method of claim 2, wherein the amino moiety of said amino-substituted alkyl sulfonic acid comprises a tertiary amine.

4. The method of claim 1, wherein the —N(R2)(R3) moiety of said amino-substituted alkyl sulfonic acid comprises a cyclic structure.

5. The method of claim 4, wherein the —N(R2)(R3) moiety of said amino-substituted alkyl sulfonic acid is selected from the group consisting of a morpholino group, a pyrrolidino group, a piperidino group, and a piperazino group.

6. The method of claim 1, wherein R1 is hydrogen and n is 1.

7. The method of claim 1, wherein R1 is hydrogen and n is 2.

8. The method of claim 1, wherein said disinfecting composition further comprises:
a water soluble carboxylic acid;
an alkaline base;
a surfactant;
a chelating agent for alkaline earth metal ions; and
a drying agent.

9. The method of claim 8, wherein said disinfecting composition further comprises FD&C Blue No. 2.

10. The method of claim 1, wherein said disinfecting composition does not contain a peroxysalt.

* * * * *